(12) United States Patent
Tamura

(10) Patent No.: US 6,295,333 B1
(45) Date of Patent: Sep. 25, 2001

(54) FLUORESCENT X-RAY ANALYZER

(75) Inventor: Koichi Tamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/359,938

(22) Filed: Jul. 22, 1999

(30) Foreign Application Priority Data

Jul. 23, 1998 (JP) .................................. 10-208261

(51) Int. Cl.$^7$ ................................................ G01N 23/223
(52) U.S. Cl. .................. 378/44; 378/45; 378/50
(58) Field of Search ................. 378/44, 45, 50

(56) References Cited

U.S. PATENT DOCUMENTS

| | | | |
|---|---|---|---|
| 4,178,513 | * | 12/1979 | Dubois et al. .......................... 378/44 |
| 4,817,120 | * | 3/1989 | Pelix et al. ............................ 378/45 |
| 4,988,872 | * | 1/1991 | Nagatsuka et al. .................. 250/310 |
| 5,187,727 | * | 2/1993 | Vogler et al. .......................... 378/50 |
| 5,299,252 | * | 3/1994 | Takahashi ............................. 378/50 |
| 5,633,908 | * | 5/1997 | Rindby et al. ....................... 378/145 |
| 5,721,759 | * | 2/1998 | Raatikainen .......................... 378/47 |
| 6,038,280 | * | 3/2000 | Rössiger et al. ...................... 378/50 |
| 6,115,450 | * | 9/2000 | Hasegawa ............................. 378/50 |
| 6,130,931 | * | 10/2000 | Laurila et al. ........................ 378/45 |

OTHER PUBLICATIONS

B. D. Cullity. Elements of X–Ray Diffraction, second edition (Reading, MA: Addison–Wesley, 1978), p. 444–446.*

* cited by examiner

Primary Examiner—Robert H. Kim
Assistant Examiner—Allen C. Ho
(74) Attorney, Agent, or Firm—Adams & Wilks

(57) ABSTRACT

An improved X-ray analyzer may be made portable and provide accurate positioning capabilities to permit precise location on a sample of a measurement point. An imaging device is provided to allow the user to observe a position at which primary X-rays generated by an X-ray source are to be irradiated onto the sample, and a display device is provided for displaying an image thereof. The display device displays a fluorescent X-ray spectrum taken at a measurement point on the sample in accordance with an output of an X-ray detector at the same time as displaying the sample image.

36 Claims, 2 Drawing Sheets

1  X RAY GENERATING SOURCE
2  COLLIMATOR
3  SAMPLE To BE MEASURED
4  X-RAY DETECTOR
5  DETECTING CIRCUIT SYSTEM
6  IMAGE COMPOSITOR
7  IMAGING DEVICE
8  MEMORY DEVICE
9  DISPLAY DEVICE
10 HOUSING
11 X-RAY EMITTING PORT

23 CIRCLE
21 X-RAY SPECTRUM
22 SCROLL CURSOR

1  X RAY GENERATING SOURCE
2  COLLIMATOR
3  SAMPLE To BE MEASURED
4  X-RAY DETECTOR
5  DETECTING CIRCUIT SYSTEM
6  IMAGE COMPOSITOR
7  IMAGING DEVICE
8  MEMORY DEVICE
9  DISPLAY DEVICE
10  HOUSING
11  X-RAY EMITTING PORT

23 CIRCLE
21 X-RAY SPECTRUM
22 SCROLL CURSOR

FLUORESCENT X-RAY ANALYZER

FIELD OF THE INVENTION

The present invention relates generally to a fluorescent X-ray analyzer capable of carrying out non-destructive element analysis, and, more particularly, to a portable fluorescent X-ray analyzer having the capability of conducting element analysis of large samples, such as archaeological samples, and performing on-site analysis in criminal investigation.

BACKGROUND INFORMATION

Conventionally, portable type X-ray analyzers have been used for the purpose of analyzing large samples or for the purpose of on-site analysis by a fluorescent X-ray analyzing method, which has an excitation source consisting of a radio isotope or an X-ray tube. Also, small X-ray analyzers such as a desktop type analyzers have been installed on vehicles wherein a sample is cut to a small enough size to be put in a sample chamber and subjected to element analysis on the vehicle.

In the conventional portable type fluorescent X-ray analyzer, it is necessary to visually align an X-ray emission port to a sample to be measured upon adjusting a relative position of a housing and a sample to be measured to specify a measuring point to which a fluorescent X-ray was irradiated. Due to this, it has been difficult to perform exact positional alignment because a point to be measured to which an X-ray is irradiated is hidden by the housing and can not be observed.

In particular, when an X-ray is irradiated onto a sample to be measured having a diameter of 10 mm or less using a collimator to restrict an X-ray light flux, positional alignment is almost impossible. The relative position of the housing and the sample to be measured are deviated by a slight amount to conduct measurements at a plurality of points and a film thickness/composition of the sample to be measured is detected, thus requiring great labor and time.

Meanwhile, in more recent years there has been an instrument in which an expensive fiver scope is attached to a housing wherein the housing mounted on a tripod is moved through a two-axis stage to effect alignment while observing the sample to be measured. There has, however, been a problem in that the entire system becomes large and heavy, thus sacrificing portability and becoming expensive.

SUMMARY OF THE INVENTION

In order to solve the above problem, a first aspect of the present invention is characterized by accommodating in a single housing an imaging device for observing a position where a primary X-ray generated by an X-ray generating source is irradiated onto a sample to be measured, and a display device for displaying an image thereof.

A second aspect of the present invention is characterized by a display, formed by superimposition or overlapping, of an X-ray spectrum at the measuring point and provided on a display device for displaying an image of the sample to measured and including a measuring point thereof.

A third aspect of the present invention is characterized in that a memory device is provided in the housing, and is further characterized in that sample images as positional information at the measuring point and corresponding X-ray spectra can be stored as a set.

By the above-described structure, in accordance with the first aspect of the invention an image of the sample to be measured is obtained by the imaging device and displayed on the display device. Accordingly, the analyzer can conduct positioning of the sample by moving either the housing or the sample, or both, to change the relative position therebetween while observing an image of the sample displayed on the display device.

In accordance with the second aspect of the present invention, because an X-ray spectrum of the sample to be measured at the measuring point obtained by the X-ray detector is displayed at the same time on the display device on which an image of the sample to be measured is displayed, it becomes quite obvious at which position sample measurement was made with an X-ray spectrum. Also, by taking a photofilm of the display device, it becomes possible to leave the image of the sample to be measured and the X-ray spectrum of the sample to be measured at the measuring point together in the image.

In accordance with the third aspect of the invention, storage in a memory device is provided for storing the image of the sample to be measured and the X-ray spectrum obtained from the sample and for the storage of the X-ray spectrum obtained from the sample as one set and for the storage of a plurality of such sets of information. Accordingly, better data control in this case is facilitated as compared to data control in the case of a single image or a single X-ray spectrum. Further, it is possible to prevent mistakes in comparing between image data and an X-ray spectrum.

DETAILED DESCRIPTION OF THE PREFERRED EMBODIMENTS

Hereinafter, an embodiment of the present invention will be explained with reference to the attached drawings.

Figure 1:
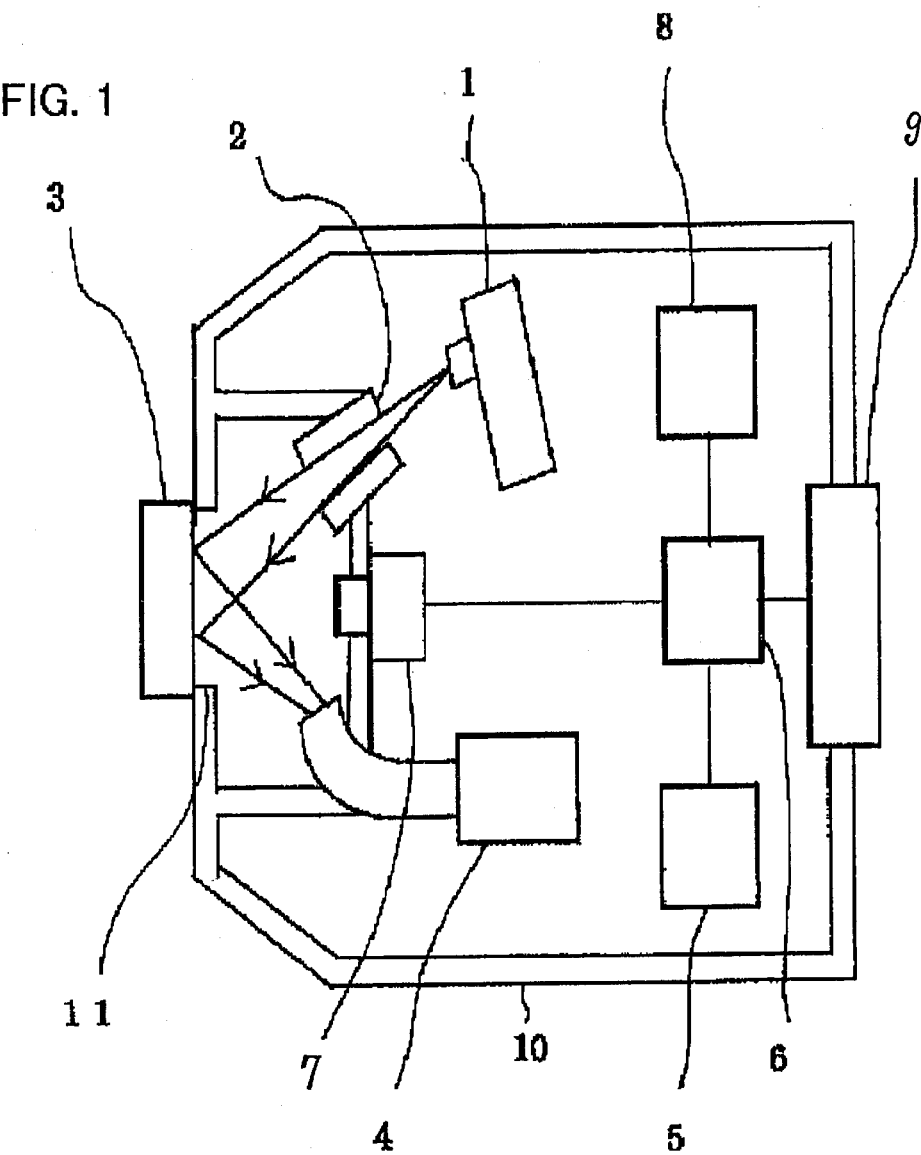
FIG. 1 is a structural view of a fluorescent X-ray analyzer showing an embodiment of the present invention.

FIG. 1 shows a structural view of a fluorescent X-ray analyzer of the present invention. A primary X-ray produced by an X-ray generating source 1 is collimated by a collimator 2, and irradiated onto a sample to be measured 3 through an X-ray emission port 11 provided in a housing 10 accommodating the aforementioned elements. The X-ray generating source 1 may comprise a radio isotope source, an X-ray tube or the like. There is no particular need to separate the collimator 2, in case that it is provided in one body in an X-ray tube housing. In FIG. 1 the sample to be measured 3 is provided on a housing side surface. However, where a sample is small like the sample illustrated in FIG. 1 and is movable, it is practical to set up the apparatus with the X-ray emission port directed upward, to rest a sample thereon and to move the sample to conduct positioning. Meanwhile, where a sample is comparatively large and fixed, e.g. such as when conducting analysis of wall paint, the apparatus is moved and aligned to a desired analysis position. Where a measurement sample is a floor surface, the sample is positioned below the apparatus and the apparatus is positioned above the sample and the apparatus is moved to conduct relative positioning. In any case, positioning is performed by changing the relative position of at least one of the measurement sample and the apparatus. As a means therefor, a camera and a display are used.

A fluorescent X-ray produced from the sample to be measured is detected by an X-ray detector 4 also accommodated within the housing 10, and then converted into an electric signal which is subjected to electric processing by a detecting circuit system 5 thus being turned into an X-ray spectrum to be expressed as energy vs. intensity. The X-ray detector can use a Si or Ge semiconductor detector, a scintillation counter, proportional counter, $HgI_2$ or the like.

An imager 7 is provided in the housing 10 and faces the X-ray emission port 11 so that an image of the sample to be measured 3 can be obtained. In a image compositor 6 electrically connected to the imager 7, a composition is made with an X-ray spectrum created by the detecting circuit system 5 and thereafter display is made on a display device 9 attached to the housing. The imager 7 can include a CCD camera, and the display device 9 may be a liquid crystal panel, a plasma display, a CRT, or the like.

Also, it is possible to structure the apparatus so as to directly display a sample image taken by the imager on the display device 9 without providing the image compositor 6.

In this manner, it becomes possible to measure a desired analysis point by moving the housing or the sample to be measured such that desired analysis point of the sample to be measured is displayed on the display device. In order to align an analysis point more closely, a measuring point adjusting method in JP-A-63-66407 is used to perform a pre-treatment process for specifying a measuring point and putting a mark at position corresponding to a measuring point to be displayed on the display device. In the measurements to be conducted thereafter, close positioning becomes possible by merely moving the housing or the sample to be measured such that a desired measuring point comes to a marked position of the display device. The means for applying such a mark at this time include methods of depicting a point or a cross cursor with a sign-pen, putting a transparent seal printed with a point or a cross cursor, and electrically displaying a cursor.

Figure 2:
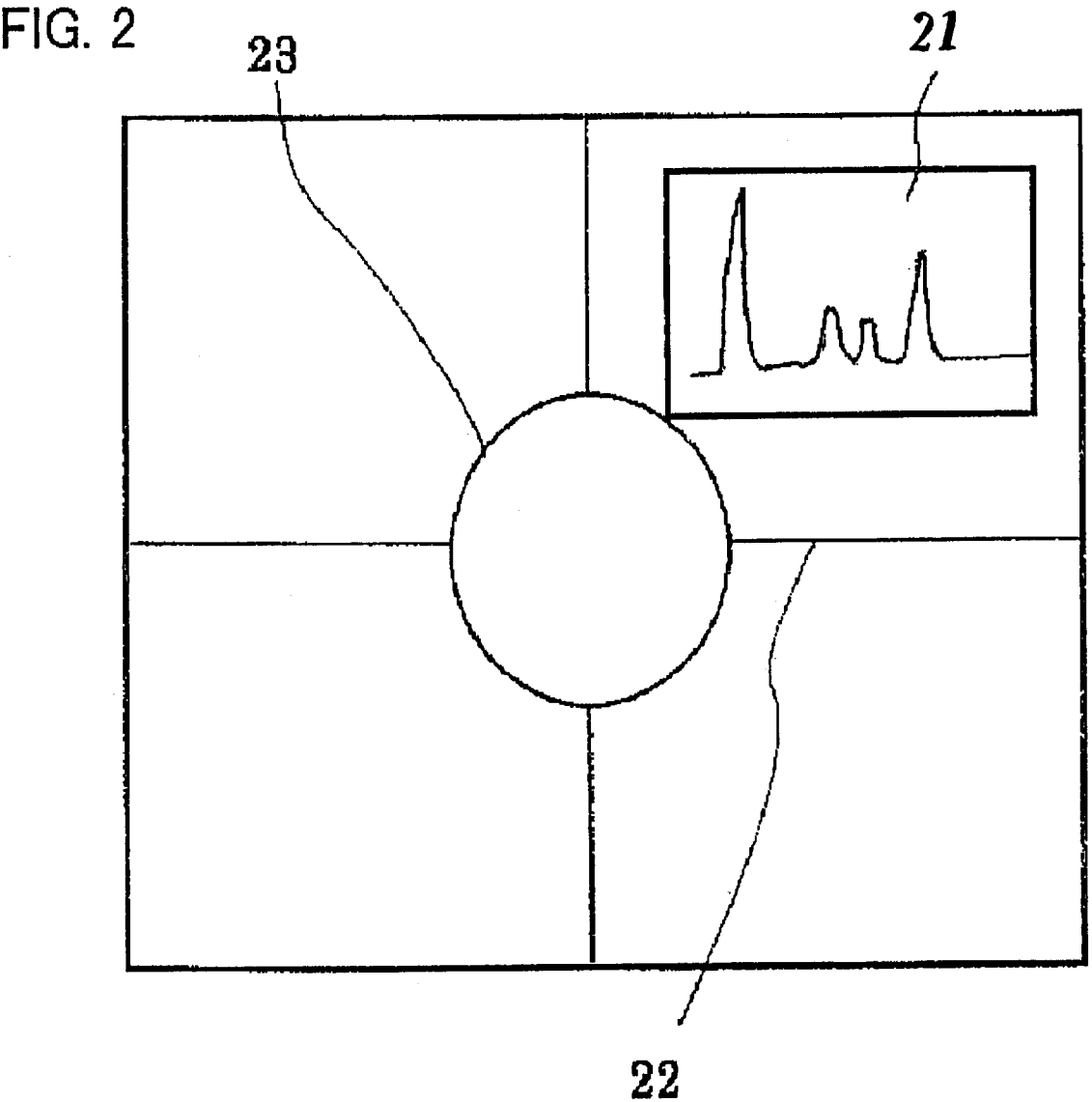
FIG. 2 is an explanatory view of a display when an X-ray spectrum is superimposed on a sample image.

On the other hand, the image and X-ray spectrum of the sample to be measured that are composited or superposed by the image compositor 6 are displayed with superimposition of overlap as shown in FIG. 2. In FIG. 2, a cross cursor 22 provides a reference to a sample position. Its center position is irradiated by a primary X-ray. An X-ray spectrum 21 at this center positional part of the sample is displayed on a screen. Also, a circle 23 is displayed to provide a reference to sample size. In FIG. 2, although an image of a sample to be measured is to be actually displayed, it is not shown herein. In the case where an image of this display is taken by a camera, image information on the sample to be measured and an X-ray spectrum can be stored together. Due to this, it can be conveniently understood at first glance from which sample an X-ray spectrum is obtained.

Also, a plurality of sets of information can be stored in a memory device 8 by storing a sample image and an X-ray spectrum as one set. Thus, data control in this case is facilitated as compared to data control of an image and a spectrum in a single form, and mistakes can be prevented when comparing an image and a spectrum.

The present invention is structured, as explained above, by accommodating in the same housing an X-ray generating source, an imaging device for observing a position where a primary X-ray generated by the X-ray generating source is irradiated onto a sample to be measured, and a display device for displaying an image thereof. There is an effect that positioning of the sample to be measured can be also made by moving either the housing or the sample to be measured or both of them to change the relative position of them while observing an image of the sample to be measured displayed on the display device.

Also, a structure is made such that an X-ray spectrum of the sample is displayed at the same time on the display device which displays a sample image, and the image and the spectrum can be stored in one set. Accordingly, an image and a spectrum can be conveniently seen at one glance. Further, there is an effect that data control such as comparison is simplified.

What is claimed is:

1. A fluorescent X-ray analyzer for performing X-ray analysis using a fluorescent X-ray method, the fluorescent X-ray analyzer comprising: an X-ray generating source; a collimator for irradiating only part of an X-ray luminous flux generated by the X-ray generating source onto a sample to be measured; an X-ray detector for detecting a fluorescent X-ray produced by the sample to be measured; an imaging device for obtaining an image of the sample to be measured; a display device for displaying the sample image; and a housing in which the X-ray generating source, the collimator, the X-ray detector, the imaging device and the display device are contained.

2. A fluorescent X-ray analyzer according to claim 1; wherein the display device displays a fluorescent X-ray spectrum taken at a measuring point on the sample in accordance with an output of the X-ray detector at the same time as displaying the sample image.

3. A fluorescent X-ray analyzer according to any one of claims 1 and 2; further comprising a memory device contained in the housing for storing one or more sets of sample images of the sample and corresponding fluorescent X-ray spectra.

4. A fluorescent X-ray analyzer according to claim 1; wherein the housing is portable so that the X-ray analyzer may be moved across a surface of a sample for performing X-ray analysis of the sample.

5. A fluorescent X-ray analyzer according to claim 1; wherein the X-ray generating source comprises an X-ray tube disposed in the housing for emitting X-rays through a window located at an end of the housing, and the housing is movable with respect to a sample to be measured for positioning of the sample with respect to X-rays generated by the X-ray tube.

6. A fluorescent X-ray analyzer according to claim 5; wherein the X-ray detector is disposed in the housing for detecting fluorescent X-rays reflected by the sample through the window.

7. A fluorescent X-ray analyzer according to claim 1; wherein the X-ray generating source uses a radioisotope for generating X-rays.

8. A fluorescent X-ray analyzer according to claim 1; wherein the X-ray detector comprises a semiconductor X-ray detector.

9. A fluorescent X-ray analyzer according to claim 8; wherein the semiconductor X-ray detector is formed of one of Si and Ge.

10. A fluorescent X-ray analyzer according to claim 1; wherein the X-ray detector comprises a scintillation counter.

11. A fluorescent X-ray analyzer according to claim 1; wherein the X-ray detector comprises a proportional counter.

12. A fluorescent X-ray analyzer according to claim 1; wherein the X-ray detector detects fluorescent X-rays using $HgI_2$.

13. A fluorescent X-ray analyzer according to claim 1; further comprising a processing circuit for converting an output of the X-ray detector into an X-ray spectrum.

14. A fluorescent X-ray analyzer according to claim 13; further comprising an image compositor connected to the imaging device and the processing circuit for receiving outputs therefrom and supplying an output to the display device for displaying the sample image and the X-ray spectrum in a superimposed manner.

15. A fluorescent X-ray analyzer according to claim 1; wherein the imaging device comprises a CCD camera.

16. A fluorescent X-ray analyzer according to claim 1; wherein the display device comprises one of a liquid crystal panel, a plasma display and a CRT.

17. A fluorescent X-ray analyzer according to claim 1; wherein the X-ray generating source and the collimator comprise an integral structure.

18. A fluorescent X-ray analyzer comprising: an X-ray generating system; X-ray detecting means for detecting X-rays emitted by the sample; a processing circuit for producing an X-ray spectrum based on the detected X-rays; an imaging device for producing an image of the sample, including a region of the sample from which the X-rays are emitted; a display device for displaying the sample image and the X-ray spectrum; a memory device for storing one or more sets of sample images and corresponding X-ray spectra; and a housing containing therein the X-ray generating system, the X-ray detecting means, the processing circuit, the imaging device, the display device and the memory device.

19. A fluorescent X-ray analyzer according to claim 18; wherein the housing is portable so that the X-ray analyzer may be moved across a surface of a sample for performing X-ray analysis of the sample.

20. A portable fluorescent X-ray analyzer comprising: an X-ray generating source for irradiating a sample with X-rays; an X-ray detector for detecting fluorescent X-rays produced by the sample in response to irradiation of the sample by the X-ray generating source; an imaging device for producing an image of the sample; a display device for displaying the sample image; and a housing in which the X-ray generating source, the X-ray detector, the imaging device and the display device are contained so that accurate sample positioning may be performed without obstruction by the housing by referring to the sample image displayed on the display device.

21. A portable fluorescent X-ray analyzer according to claim 20; further comprising a collimator contained in the housing for collimating X-rays generated by the X-ray generating source and projecting the X-rays onto the sample.

22. A portable fluorescent X-ray analyzer according to claim 21; wherein the X-ray generating source and the collimator comprise an integral structure.

23. A portable fluorescent X-ray analyzer according to claim 20; further comprising a processing circuit for producing an X-ray spectrum in accordance with an output of the X-ray detector; wherein the display device provides a display of the sample image and the X-ray spectrum.

24. A portable fluorescent X-ray analyzer according to claim 23; wherein the display device provides a simultaneous display of the sample image and the X-ray spectrum.

25. A portable fluorescent X-ray analyzer according to claim 20; wherein the X-ray generating source comprises an X-ray tube disposed in the housing for emitting X-rays through a window located in the housing, and the housing is movable with respect to a sample to be measured for positioning of the sample with respect to X-rays generated by the X-ray tube.

26. A portable fluorescent X-ray analyzer according to claim 25; wherein the X-ray detector is disposed in the housing for detecting fluorescent X-rays reflected by the sample through the window.

27. A portable fluorescent X-ray analyzer according to claim 20; wherein the X-ray generating source uses a radioisotope for generating X-rays.

28. A portable fluorescent X-ray analyzer according to claim 20; wherein the X-ray detector comprises a semiconductor X-ray detector.

29. A portable fluorescent X-ray analyzer according to claim 28; wherein the semiconductor X-ray detector is formed of one of Si and Ge.

30. A portable fluorescent X-ray analyzer according to claim 20; wherein the X-ray detector comprises a scintillation counter.

31. A portable fluorescent X-ray analyzer according to claim 20; wherein the X-ray detector comprises a proportional counter.

32. A portable fluorescent X-ray analyzer according to claim 20; wherein the X-ray detector detects fluorescent X-rays using $HgI_2$.

33. A portable fluorescent X-ray analyzer according to claim 20; further comprising a processing circuit for converting an output of the X-ray detector into an X-ray spectrum.

34. A portable fluorescent X-ray analyzer according to claim 33; further comprising an image compositor connected to the imaging device and the processing circuit for receiving outputs therefrom and supplying an output to the display device for displaying the sample image and the X-ray spectrum as a single image.

35. A portable fluorescent X-ray analyzer according to claim 20; wherein the imaging device comprises a CCD camera.

36. A portable fluorescent X-ray analyzer according to claim 20; wherein the display device comprises one of a liquid crystal panel, a plasma display and a CRT.

* * * * *